United States Patent
Averina

(10) Patent No.: US 10,078,731 B2
(45) Date of Patent: Sep. 18, 2018

(54) SYSTEM AND METHODS FOR DISPLAYING MEDICAL DATA

(71) Applicant: Cardiac Pacemakers, Inc., St. Paul, MN (US)

(72) Inventor: Viktoria A. Averina, Shoreview, MN (US)

(73) Assignee: Cardiac Pacemakers, Inc, St. Paul, MN (US)

( * ) Notice: Subject to any disclaimer, the term of this patent is extended or adjusted under 35 U.S.C. 154(b) by 116 days.

(21) Appl. No.: 15/057,798

(22) Filed: Mar. 1, 2016

(65) Prior Publication Data

US 2016/0259910 A1    Sep. 8, 2016

Related U.S. Application Data

(60) Provisional application No. 62/129,288, filed on Mar. 6, 2015.

(51) Int. Cl.
   G06F 19/00    (2018.01)
   G06T 11/20    (2006.01)
   (Continued)

(52) U.S. Cl.
   CPC ........ G06F 19/3443 (2013.01); G06T 11/206 (2013.01); G16H 10/60 (2018.01);
   (Continued)

(58) Field of Classification Search
   None
   See application file for complete search history.

(56) References Cited

U.S. PATENT DOCUMENTS

| 5,447,164 A | 9/1995 | Shaya et al. |
| 2005/0162423 A1 | 7/2005 | Goggin |

(Continued)

FOREIGN PATENT DOCUMENTS

WO    WO-2016144612 A1    9/2016

OTHER PUBLICATIONS

Cleveland, William S., "A Model for Studying Display Methods of Statistical Graphics", Journal of Computational and Graphical Statistics, vol. 2, No. 4, [Online]. Retrieved from the Internet: <URL: http://www.jstor.org/stable/1390686, (Dec. 1993), 323-343.

(Continued)

*Primary Examiner* — Edward Martello
(74) *Attorney, Agent, or Firm* — Schwegman Lundberg & Woessner, P.A.

(57) ABSTRACT

Systems and methods for displaying medical or physiologic data are disclosed. The system can receive medical data such as a physiologic trend indicative of worsening of heart failure. The system can generate a graphical representation of the medical data in a two-dimensional or a higher-dimensional coordinate space. The graphical representation can include line segments indicating temporal variation of the medical data. The system can determine a desired range, including lower and upper bounds, for displaying the medical data using signal statistics and a correction factor, and specified number of tickmarks between the desired LB and UB. The desired lower and upper bounds can enhance visual perception of temporal variation of the medical data, and thus to facilitate data interpretation and clinical decision making. A display unit can display the graphical representation of the medical data within the desired lower and upper bounds.

20 Claims, 6 Drawing Sheets

(51) Int. Cl.
*G16H 10/60* (2018.01)
*G16H 50/70* (2018.01)
*G16H 40/63* (2018.01)
*G16H 15/00* (2018.01)

(52) U.S. Cl.
CPC .............. *G16H 50/70* (2018.01); *G16H 15/00* (2018.01); *G16H 40/63* (2018.01)

(56) References Cited

U.S. PATENT DOCUMENTS

| | | |
|---|---|---|
| 2010/0030302 A1 | 2/2010 | Blowers et al. |
| 2010/0145170 A1 | 6/2010 | Ayers et al. |
| 2012/0203166 A1 | 8/2012 | Riback et al. |
| 2015/0061889 A1* | 3/2015 | Kotaki .................. G06T 11/206 340/870.05 |
| 2015/0273147 A1* | 10/2015 | Duke .................. A61M 5/1723 604/504 |

OTHER PUBLICATIONS

"International Application Serial No. PCT/US2016/020243, International Preliminary Report on Patentability dated Sep. 21, 2017", 9 pgs.
"International Application Serial No. PCT/US2016/020243, International Search Report dated Jul. 18, 2016", 6 pgs.
"International Application Serial No. PCT/US2016/020243, Written Opinion dated Jul. 18, 2016", 8 pgs.
Kovatchev, B, et al., "Symmetrization of the blood glucose measurement scale and its applications", Diabetes Care, American Diabetes Association, (Nov. 1, 1997), 1655-1658 pgs.
Maindonald, John, et al., "Styles of data analysis", Data Analysis and Graphics using R—An Example-Based Approach (3rd Edition), (Jan. 1, 2010), 43-76 pgs.

* cited by examiner

SYSTEM AND METHODS FOR DISPLAYING MEDICAL DATA

CLAIM OF PRIORITY

This application claims the benefit of priority under 35 U.S.C. § 119(e) of U.S. Provisional Patent Application Ser. No. 62/129,288, filed on Mar. 6, 2015, which is herein incorporated by reference in its entirety.

TECHNICAL FIELD

This document relates generally to medical systems, and more particularly, but not by way of limitation, to systems for displaying medical or physiologic data.

BACKGROUND

Medical systems or medical devices can acquire medical or physiologic data from a subject. The acquired data can be displayed in real time, or be stored in a designated storage device and retrieved for monitoring at a later time. By review the data, healthcare professionals can make diagnostic or therapeutic decisions based at least in part on visual inspection and interpretation of the displayed data.

Clinicians can base their clinical decision on trended medical data, such as measurements of a physiologic parameter over a period of time. The trended medical data can be displayed in different scales to facilitate visual inspection of the data change over tune. A properly selected data range can enhance the accuracy of data interpretation.

Overview

Efficient and accurate visual presentation of medical or physiologic data, such as a chart or graph of temporal variation of data intensity, can be important for clinicians to make initial decisions of diagnosis or treatment. Traditionally, the data such as physiologic trend can be displayed in a fixed range, such that the signal intensity is bounded by a fixed display range. This can often obscure a significant change in the data, and make visual interpretation of data difficult, or result in inaccurate interpretation. Fixed-range data presentation can also be less optimal when substantial inter-patient variation exists due to different anatomical or physiologic conditions across patients, or different system configurations adopted for data acquisition from different patients.

One alternative to the fixed-range display is an adjustable range, such as a system functionality that allows a system user to "zoom in" or "zoom out" a particular portion of the displayed data. Such operations, however, may not be sufficient, such as when the signal is contaminated by noise or interference that cannot be effectively removed or substantially reduced using techniques such as filtering. For example, simple operation of zooming in the data may exaggerate the noise content, thereby making it difficult to visually identify the signal change or other useful information contained in the data.

For trended medical or physiologic data, the displayed data can usually include line segments that represent or approximate the changes in the data. Because the human visual system is very sensitive to line orientations, the relative orientation of line segments can strongly impact a user's perception of trends in the data. William Cleveland has described a relationship between an aspect ratio (defined as a ratio between the width and the height of a chart containing the line segments) and the graphical perception. (See, William S. Cleveland, "A Model for Studying Display Methods of Statistical Graphics", Journal of Computational and Graphical Statistics, Vol. 2, No. 4, December, 1993. pp. 323-343.) Cleveland introduces a technique known as "banking to 45 degrees" that determines the aspect ratio such that the average orientation of all line segments in a chart is at 45 degrees, one the notion that an orientation of 45 degrees can maximize the visual discriminability of adjacent line segments.

Because the height of a chart is related to the range of the displayed data, by changing the aspect ratio, the "banking to 45 degrees" method can be used to find an aspect ratio that that enhances visual data interpretation. However, since the method is an optimization based on line segments, and the line segments can be susceptible to noise or interference, the resulting data range may not be ideal when the medical data are noisy. Moreover, in various medical applications such as medical data reports and presentation, the aspect ratio of a plot has to be fixed and cannot be adjusted based on the particular data being displayed. The present inventors have thus recognized that there remains a need to improve the method of displaying medical or physiologic data, including determining an ideal data range rather than the aspect ratio for data display, so as to enhance visual perception of the information contained in the data such as signal change.

This document discusses, among other things, systems and methods for displaying medical or physiologic data. A system can receive and process medical or physiologic data, such as a physiologic trend, and generate a graphical representation of the medical data in a two-dimensional or a higher-dimensional coordinate space. The system can determine an upper bound and a lower bound for one of the axes given bounds on all the remaining axes for displaying the medical data by using signal statistics and a correction factor, and display the graphical representation of the medical data within the desired lower and upper bounds. The lower and upper bounds thus determined can improve visual perception of the temporal variation of the medical data to facilitate data interpretation or medical diagnosis.

Example 1 can include a system for displaying medical or physiologic data. The system can comprise an input circuit, a processor circuit, and a display unit. The input circuit can be configured to receive medical or physiologic data. The processor circuit can generate a graphical representation of the medical or physiologic data in a two-dimensional or a higher-dimensional coordinate space. The graphical representation can include line segments indicating temporal variation of the medical or physiologic data. The processor circuit can determine a desired range of at least one axis for displaying the medical or physiologic data including determining a desired lower bound (LB) and a desired upper bound (UB) using an initial signal statistical parameter and a correction factor. The correction factor can be computed using at least one of a signal range of the received medical or physiologic data, a specified number of tickmarks for the at least one axis, or a noise level of the received medical or physiologic data. The display unit, which can be coupled to the processor unit, can display in the coordinate space the graphical representation of the medical or physiologic data within the desired range.

Example 2 can include, or can optionally be combined with the subject matter of Example 1 to optionally include, the processor circuit which can be further configured to generate a specified number (TN) of tickmarks equally spaced between the desired LB and UB and symmetric around a center between the desired LB and UB. The tickmarks can be indicative of respective intermediate levels between the LB and UB. The display unit can be configured to display the specified number of tickmarks.

Example 3 can include, or can optionally be combined with the subject matter of one or a combination of Examples 1 through 2 to optionally include, the medical or physiologic data that can include a physiologic trend signal. The processor circuit can be configured to generate a graphical representation of the physiologic trend signal in a two-dimensional coordinate space.

Example 4 can include, or can optionally be combined with the subject matter of one or any combination of Examples 1 through 3 to optionally include, the initial signal statistical parameter that can include an initial central tendency measure ($C_0$) of a specified portion of the medical or physiologic data to be displayed.

Example 5 can include, or can optionally be combined with the subject matter of one or any combination of Examples 2 through 4 to optionally include, the processor circuit that can be further configured to receive a plurality of candidate tickmark steps (CTSs), and to determine a selected tickmark step (TS) from the plurality of CTSs. The selected tickmark step TS can be the smallest among the CTSs that satisfies CTS>R/α, wherein R indicates a range of the specified portion of the medical or physiologic data and α is a scaling factor determined using TN and a specified fractional offset (d).

Example 6 can include, or can optionally be combined with the subject matter of one or any combination of Examples 2 through 4 to optionally include, the processor circuit that can be configured to determine an initial tickmark step $TS_0$=R/α, wherein α is a scaling factor determined using TN and a specified fractional offset (d). The processor circuit can be configured to determine a selected tickmark step (TS) including rounding the initial tickmark step $TS_0$ to a nearest multiple of a specified base resolution (BR), the nearest multiple of BR greater than $TS_0$.

Example 7 can include, or can optionally be combined with the subject matter of Example 6 to include, the processor circuit that can be configured to determine the correction factor δ as δ=TS*α, and to determine the LB as LB=C−δ and the UB as UB=C+δ, where C is an updated central tendency measure of the specified portion of the medical or physiologic data to be displayed.

Example 8 can include, or can optionally be combined with the subject matter of Example 4 to include, the processor circuit that can be further configured to determine an updated central tendency C including rounding the initial central tendency measure $C_0$ to a nearest multiple of a selected base resolution (BR).

Example 9 can include, or can optionally be combined with the subject matter of Example 5 to include, the processor circuit that can be further configured to receive a plurality of candidate base resolution (CBRs), each CBR corresponding to a respective candidate tickmark step in the CTSs. The processor circuit can be configured to determine a selected base resolution (BR) among the plurality of CBRs corresponding to the selected IS, and determine an updated central tendency C including rounding the $C_0$ to a nearest multiple of the BR.

Example 10 can include, or can optionally be combined with the subject matter of one or any combination of Examples 8 and 9 to include, the processor circuit that can generate the specified number (IN) of tickmarks which can include a first tickmark T1 and a second tickmark T2, to determine the correction factor δ as δ=TS*d, and to determine the LB as LB=T1−δ and the UB as UB=T2+δ. The first tickmark T1 and the second tickmark T2 can be determined as one of the following: T1 is at C−TS*(TN−1)/2 and T2 is at C+TS*(TN−1)/2, T1 is at a specified value LTS, and T2 is at LTS+TS*(TN−1); or T2 is at a specified value UTS, and T1 is at UTS−TS*(TN−1).

Example 11 can include, or can optionally be combined with the subject matter of one or any combination of Examples 1 through 10 to include, a noise analyzer circuit and a line segment analyzer circuit. The noise analyzer circuit can be configured to determine a noise level using the medical or physiologic data, and to determine a noise-based range using at least the noise level, the noise-based range including at least one of a noise-based lower bound ($L_N$) or a noise-based upper bound ($U_N$). The line segment analyzer circuit can be configured to generate a plurality of line segments using the medical or physiologic data, and to determine a signal-based range using the plurality of line segments. The signal-based range can include at least one of a signal-based lower bound ($L_S$) or a signal-based upper bound ($U_S$). The processor circuit is configured to determine the desired range including the desired lower bound LB or the desired upper bound UB using one or more of $L_N$, $U_N$, $L_S$, or $U_S$.

Example 12 can include, or can optionally be combined with the subject matter of Example 11 to include, an initial lower bound $L_0$ and an initial upper bound $U_0$, and a first correction factor $δ_1$ and a second correction factor $δ_2$. The $L_0$ can indicate a minimal value of a specified portion of the medical or physiologic data, and $U_0$ can indicate a maximal value of the specified portion of the medical or physiologic data. The first and second correction factors $δ_1$ and $δ_2$ can each be determined using the noise level. The noise analyzer circuit can determine the noise-based lower bound $L_N$ using an initial lower bound $L_0$ and a first correction factor $δ_1$, or to determine the noise-based upper bound $U_N$ using an initial upper bound $U_0$ and a second correction factor $δ_2$.

Example 13 can include, or can optionally be combined with the subject matter of one or any combination of Examples 11 or 12 to include the processor circuit that can be configured to generate the plurality of line segments fitted to specified portions of the medical or physiologic data to be displayed.

Example 14 can include, or can optionally be combined with the subject matter of one or any combination of Examples 11 or 13 to include the line segment analyzer circuit that can determine for one or more of the line segments respective one or more line-segment slopes, wherein the line-segment slopes can be indicative of an orientation (θ) of the respective line segment. The line segment analyzer circuit can also compute a composite orientation ($θ_{Avg}$) using the one or more line-segment slopes corresponding to the plurality of the line segments, and determine at least one of the signal-based lower bound ($L_S$) or the signal-based upper bound ($U_S$) in response to the composite orientation ($θ_{Avg}$) meeting a specified criterion.

Example 15 can include, or can optionally be combined with the subject matter of one or any combination of Examples 11 through 14 to include the processor circuit that can determine the LB to be $L_N$ and the UB to be $U_N$ when $R_N$ is greater than $R_S$, and to determine the LB to be $L_S$ and the UB to be $U_S$ when $R_S$ is greater than $R_N$.

Example 16 can include a method for displaying medical or physiologic data. The method can comprise operations of receiving medical or physiologic data, and generating a graphical representation of the medical or physiologic data in a two-dimensional or a higher-dimensional coordinate space. The coordinate space can include a time coordinate, and the graphical representation can include line segments indicating temporal variation of the medical or physiologic data. The method can also comprise determining a desired range of at least one axis for displaying the medical or physiologic data, including determining a desired tower bound (LB) and a desired upper bound (UB) using an initial signal statistical parameter and a correction factor (δ), and displaying in the coordinate space the graphical representation of the medical or physiologic data within the desired range on a display unit. The correction factor can be computed using at least one of a signal range of the received medical or physiologic data, a specified number of tickmarks for the at least one axis, or a noise level of the received medical or physiologic data.

Example 17 can include, or can optionally be combined with the subject matter of Example 16 to optionally include, an operation of generating a specified number (TN) of tickmarks equally spaced between the desired LB and UB and symmetric around a center between the desired LB and UB, and displaying the specified number tickmarks on a display unit.

Example 18 can include, or can optionally be combined with the subject matter of Example 17, to optionally include the initial signal statistical parameter which can include an initial central tendency measure ($C_0$) of a specified portion of the medical or physiologic data to be displayed.

Example 19 can include, or can optionally be combined with the subject matter of Example 17, to optionally include operations of receiving a plurality of candidate tickmark steps (CTSs), and determining a selected tickmark step (TS) from the plurality of CTSs. The selected tickmark step TS can be the smallest among the CTSs that satisfies CTS>Rα, wherein R indicates a range of the specified portion of the medical or physiologic data and α is a scaling factor determined using TN and a specified fractional offset (d).

Example 20 can include, or can optionally be combined with the subject matter of Example 19, to optionally include operations of: receiving a plurality of candidate base resolution (CBRs), each CBR corresponding to a respective candidate tickmark step in the CTSs; determining, among the plurality of CBRs, a selected base resolution (BR) corresponding to the selected TS; determining an updated central tendency C including rounding the $C_0$ to a nearest multiple of the BR; generating the specified number (TN) of tickmarks including a first tickmark T1 a second tickmark T2; determining the correction factor δ as δ=TS*d; and determining the LB as LB=T1−TS*d and the UB as UB=T2+TS*d. The first tickmark T1 and the second tickmark T2 can be determined as one of the following: T1 is at C−TS*(TN−1)/2 and T2 is at C+TS*(TN−1)/2; T1 is at a specified value LTS, and T2 is at LTS+TS*(TN−1); or T2 is at a specified value UTS, and T1 is at UTS−TS*(TN−1).

Example 21 can include, or can optionally be combined with the subject matter of Example 16, to optionally include operations of determining a noise level using the medical or physiologic data, determining a noise-based range using at least the noise level, the noise-based range including at least one of a noise-based lower bound ($L_N$) or a noise-based upper bound ($U_N$), generating a plurality of line segments using the medical or physiologic data, determining a signal-based range using the plurality of line segments, the signal-based range including at least one of a signal-based lower bound ($L_S$) or a signal-based upper bound ($U_S$), and determining the desired range including the desired lower bound LB or the desired upper bound UB using one or more of $L_N$, $U_N$, or $U_S$.

Example 22 can include, or can optionally be combined with the subject matter of Example 21, to optionally include determining for one or more of the line segments respective one or more line-segment slopes, the line slopes indicative of an orientation (θ) of the respective line segment, computing a composite orientation ($\theta_{Avg}$) using the one or more line-segment slopes corresponding to the plurality of the line segments, and determining at least one of the signal-based lower bound ($L_S$) or the signal-based upper bound ($U_S$) in response to the composite orientation ($\theta_{Avg}$) meeting a specified criterion.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for medical or physiologic data display. According to the present document, a system can process medical data to generate a graphical representation, including line segments, in a two-dimensional or a higher-dimensional coordinate space. A desired range, including lower and upper bounds, for one of the axes for displaying the medical data can be generated by using signal statistics and a correction factor. The lower and upper bounds are determined to improve visual perception of temporal variation of the medical data to facilitate data interpretation or medical diagnosis. One or more tickmarks can also be determined based on signal statistics. The graphical representation of the medical data can be displayed on a display unit within the desired lower and upper bounds.

Figure 1:
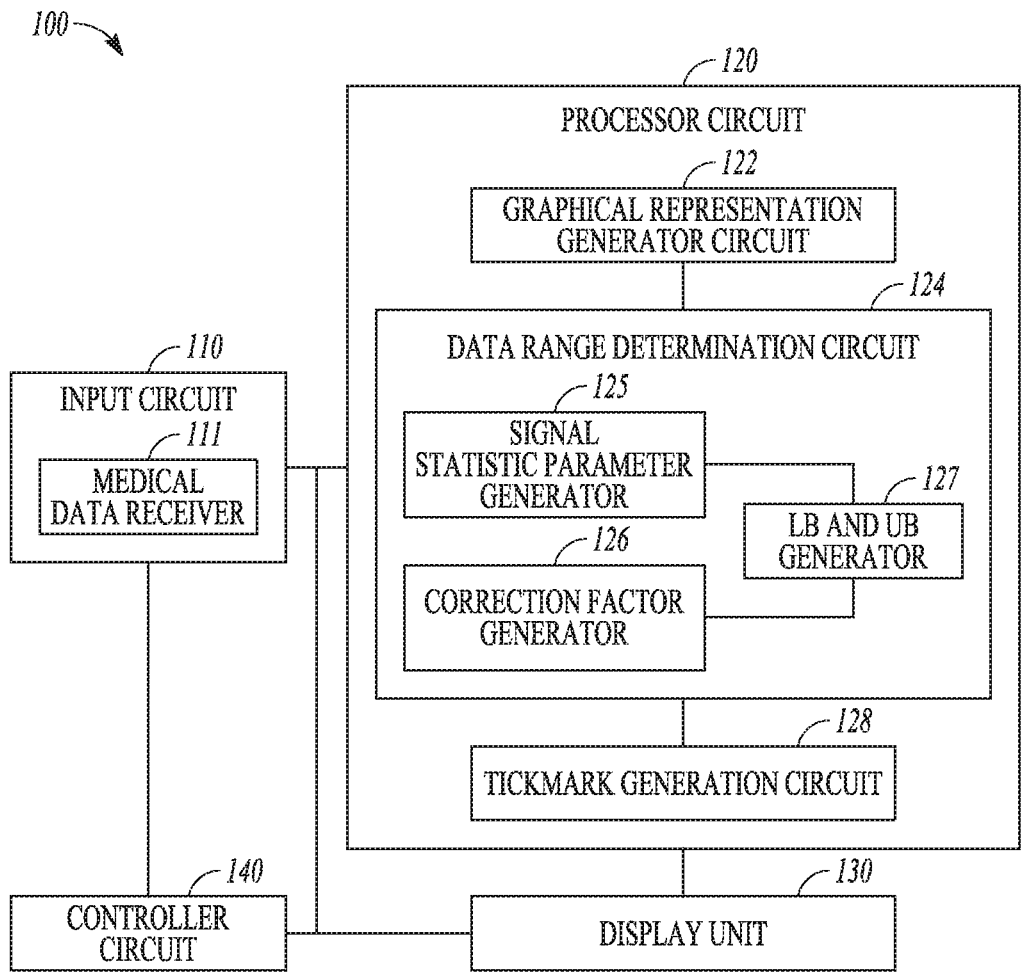
FIG. 1 illustrates an example of a medical data presentation system.

FIG. 1 illustrates an example of a medical data presentation system 100, which can include one or more of an input circuit 110, a processor circuit 120, a display unit 130, and a controller circuit 140.

The input circuit 110 can include a medical data receiver 111 that is configured to receive medical or physiologic data of a subject. The medical or physiologic data can be indicative of the subject's physiologic or pathologic conditions or general health status, and can be used to generate diagnostic or therapeutic decisions. The medical or physiologic data can include a trend comprising data obtained at different time instants or time intervals. In an example, the medical data receiver 111 can receive physiologic signals indicative of worsening of heart failure (HF), such as an event of heart failure decompensation. Examples of the physiologic signals can include one or more of electrocardiogram, intracardiac electrogram, arrhythmia, heart rate signal, heart rate variability signal, intrathoracic impedance signal, intracardiac impedance signal, arterial pressure signal, pulmonary artery pressure signal, left atrial pressure signal, RV pressure signal, LV coronary pressure signal, coronary blood temperature signal, blood oxygen saturation signal, one or more heart sounds signal, physical activity or exertion level signal, physiologic response to activity, posture, respiration signal, body temperature measurements, weight, among other physiologic signals.

In an example, the medical data receiver 111 can be coupled to one or more implantable, wearable, or otherwise ambulatory sensors associated with the subject. Examples of such sensors can include electrodes for sensing cardiac electrical activities such as surface electrocardiography (ECG) or subcutaneous ECG, intracardiac or transvenous electrodes for sensing intracardiac electrogram (EGM), bioimpedance sensors, pressure sensors, chemical sensors, ambulatory accelerometer or acoustic sensors, among others.

In an example, the medical data receiver 111 can be coupled to a storage device such as an electronic medical record (EMR) system, and retrieve from the storage device one or more patient historical physiologic signals in response to a command signal. The command signal can be issued by a system user such as a clinician, or generated automatically by the system in response to a specified event. The medical data receiver 111 can include one or more sub-circuits that can perform signal conditioning or pre-processing, including signal amplification, digitization, or filtering, on the one or more physiological signals.

The processor circuit 120 can be configured to generate a human-perceptible presentation of the received medical or physiologic data. The processor circuit 120 can be implemented as a part of a microprocessor circuit within the medical data presentation system 100. The microprocessor circuit can be a dedicated processor such as a digital signal processor, application specific integrated circuit (ASIC), microprocessor, or other type of processor for processing information including physical activity information. Alternatively, the microprocessor circuit can be a general purpose processor that can receive and execute a set of instructions of performing the functions, methods, or techniques described herein.

The processor circuit 120 can include a graphical representation generator circuit 122 and a data range determination circuit 124. The processor circuit 120 can optimally include a tickmark generation circuit 128. The graphical representation generator circuit 122 can be configured to generate a graphical representation of the received medical or physiologic data in a two-dimensional or a higher-dimensional coordinate space. The coordinate space can include at least a time coordinate. In an example, the received medical data can include a physiologic signal or trend, and the graphical representation generator circuit 122 can generate the graphical representation in a two-dimensional coordinate space spanned by a time axis and a signal intensity axis. In an example, the received medical data include physiologic signal intensity information measured at different time or at different locations (such as different sites on heart), and the graphical representation generator circuit 122 can generate the graphical representation in a three-dimensional coordinate space spanned by a time axis, a spatial location axis (such as a distance from a specified site in the heart), and a signal intensity axis.

The graphical representation can comprise line segments indicating temporal variation of the received medical or physiologic data. Because the received medical or physiologic data can usually be discrete samples, the line segments can provide a visual perception of continuous variation of the underlying physiologic parameter. The line segments can therefore facilitate interpretation of the medical data. In an example where the received medical data includes physiologic trend, the graphical representation generator circuit 122 can generate line segments using interpolation between measured samples of the physiologic trend. In an example, the graphical representation generator circuit 122 can generate line segments using curve-fitting of two or more measured samples of the physiologic trend. Examples of generating the line segments using curve fitting are described below, such as with reference to FIG. 4.

The data range determination circuit 124 can be configured to determine a desired range of at least one axis for displaying the medical data. The desired range can include one or both of a desired lower bound (LB) and a desired upper bound (UB). The LB and the UB can define the range for displaying the medical data at the specified axis. For example, when the received medical data includes physiologic trend, the data range determination circuit 124 can determine a lower bound and an upper bound for the signal intensity, such that the physiologic trend can be displayed within a range defined by the lower and upper bounds.

In an example, the data range determination circuit 124 can determine the desired range, such as the LB and the UB, in a recursive approach. As illustrated, the data range determination circuit 124 can include a signal statics parameter generator 125 and a correction factor generator 126. The signal statics parameter generator 125 can generate an initial signal statistical parameter. In an example, the initial signal statistical parameter can include a central tendency estimate of a specified portion of the medical data. In another example, the initial signal statistical parameter can include maximal or minimal of a specified portion of the medical data. The initial signal statistical parameter can be used to generate initial desired bounds such as the LB and the UB. The correction factor generator 126 can produce a correction factor for use to expand, reduce, or otherwise modify the initial desired bounds. The lower and upper bounds generator 127 can then use the signal statics parameters and the correction factors to generate the desired LB and UB. Examples of the data range determination circuit 124 are described below, such as with reference to FIGS. 2-3.

The tickmark generation circuit 128 can be configured to generate a plurality of tickmarks at one or more specified locations between the LB and the UB. The tickmarks can include a graphical mark, and additionally or alternatively a numerical indicator indicating intermediate levels of intensity of the medical data between the LB and UB. In an example, the number (TN) of tickmarks can be independent of the LB or the UB. For example, the data range determination circuit 122 can determine a first data range including $LB_1$ and $UB_1$ for a first physiologic trend, and a second range including $LB_2$ and $UB_2$ for a different second physiologic trend. The tickmark generation circuit 128 can generate the same number of tickmarks for both the first data range ($LB_1$ and $UB_1$) and the second data range ($LB_2$ and $UB_2$). In an example, at least three tickmarks can be generated, including a center tickmark located at or near the center between the LB and the UB, a tickmark at or near the LB, and a tickmark at or near the UB. Examples of the tickmark generation, such as the intermediate levels associated with each tickmark, are described below, such as with reference to FIG. 2.

The display unit 130 can be coupled to the processor unit 120, and configured to display in the coordinate space the graphical representation of the medical data within the desired range, such as between the desired lower bound LB and the desired upper bound UB. The display unit 130 can further be configured to display one or more of the tickmarks such as generated by the tickmark generation circuit 128. The display unit 130 can further display one or more grid lines respectively originating at or crossing the plurality of tickmarks. In some examples, the display unit 130 can include a user interface that allows a user to interactively selecting a portion of the display data, adjusting or resealing the display zone, highlighting a portion of the displayed data, adding note at a specified region in the display zone, or performing other operations on the display unit 130.

The display unit 130 can include a monitor screen for displaying the medical data and optionally the tickmark information. The display unit 130 can be physically integrated with the processor circuit 120 in a device such as a mobile device (e.g., portable computer, smart phone, or tablet) or other type of computer (e.g., a medical device programmer) that communicates wirelessly or via wired connection with the input circuit. Alternatively, the display unit 130 can be physically separated from and communicatively coupled to the processor circuit 120. In an example, the processor circuit 120 can be a part of a remote server, bedside monitor, or other type of monitoring device, and the display unit 130 can include a mobile device or a traditional computer monitor. The data processor circuit 120 can transmit the medical data and optionally the tickmark information to the display unit 130 via an established communication link.

The controller circuit 140 can control the operations of the input circuit 110, the processor circuit 120, the display unit 130, and the data flow and instructions between these components and respective subcomponents. In an example, the controller circuit 140 can receive from the input circuit 110 which can be configured to receive user instructions for operating the medical data presentation system TOO. Examples of the user instructions can include acquisition and preprocessing of the medical or physiologic data, generation of line segments from the medical data, determination of the data range, generation of tickmarks, and display of the medical data and the tickmarks.

Figure 2:
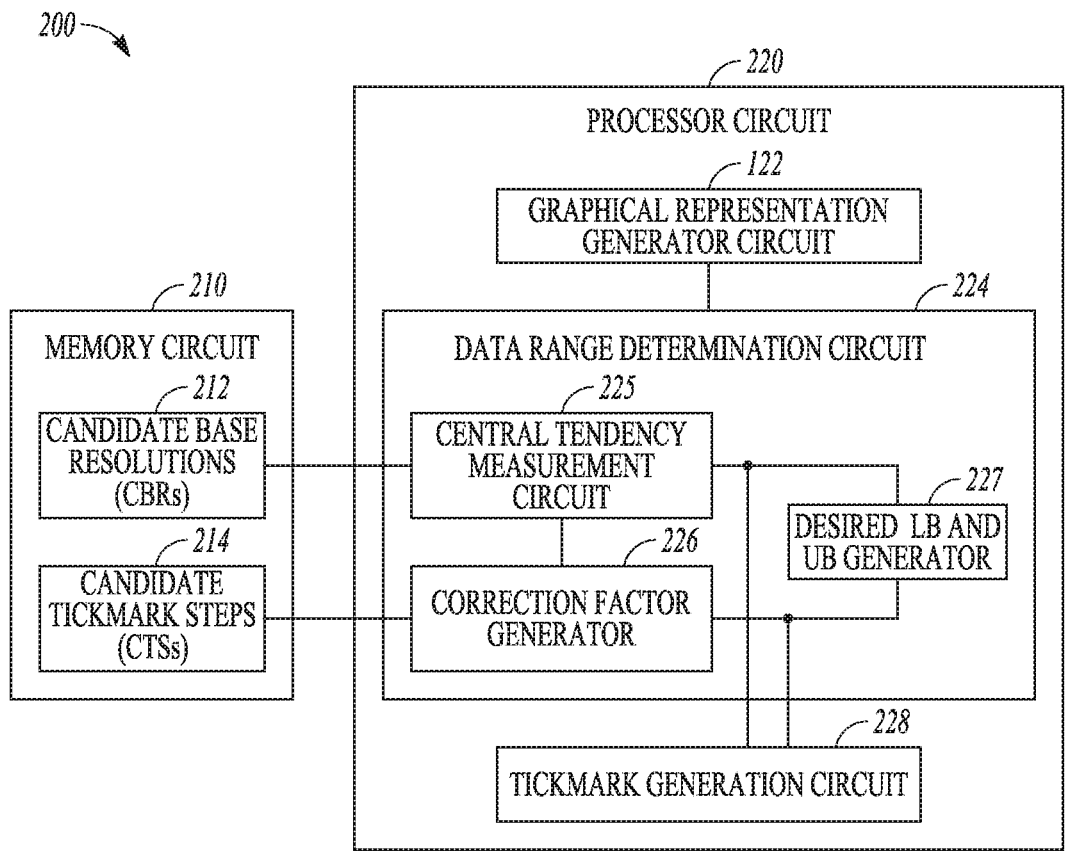
FIG. 2 illustrates an example of portions of a medical data presentation system.

FIG. 2 illustrates an example of portions of a medical data presentation system 200, which can be an embodiment of the medical data presentation system 100. The medical data presentation system 200 can comprise a memory circuit 210, and a processor circuit 220 which can be an embodiment of the processor circuit 120.

The memory circuit 210 can store a set of candidate base resolutions (CBRs) 212 and a corresponding set of candidate tickmark steps (CTSs) 214. The CTSs 214 can include a plurality of values that each indicating a step size (e.g., a minimal change) at the corresponding tickmark. For example, a candidate tickmark step of 0.2 indicates that the difference between two adjacent tickmarks can be a multiple of 0.2. The candidate base resolutions 212 can include a plurality of values that indicate a base resolution at the center of the tickmark. Each CBR can correspond to a particular CTS. For example, a base resolution of 0.1 indicates that the allowed resolution on the center tickmark is 0.1. In an example, the number of candidate tickmark steps equals the number of the candidate base resolutions. Both the CTS and the BR can be pre-determined or specified by a system user and stored in the memory circuit 210.

The processor circuit 220 can include the graphical representation generator circuit 122, a data range determination circuit 224, and a tickmark generation circuit 228. The data range determination circuit 224, which cat b an embodiment of the data range determination circuit 124, can include a central tendency measurement circuit 225, a correction factor generator circuit 226, and a desired lower bound (LB) and upper bound (UB) generator 227. The central tendency measurement circuit 225, which can be an embodiment of the signal statistic parameter generator 125, can generate an initial central tendency measure ($C_0$) from the received medical or physiologic data. Examples of the central tendency measures can include mean, median, mode, among others. In an example, the central tendency measure can be computed as an average of the minimum and the maximum of a specified portion of the medical data (X), that is, $C_0 = \max(X) + \min(X))/2$.

The correction factor generator circuit 226 can select, from the plurality of CTS, a selected tickmark step (TS) when TS meets a specified criterion. The correction factor generator circuit 226 can compare the CTSs to a range (R) of the specified portion of the medical data, and determine the TS to be the smallest among the CTSs when the comparison meets a specified criterion. In an example, the correction factor generator circuit 226 can select TS for a specified portion of the medical data in a two-step process. First, a subset of the CTSs can be selected, which include CTSs that meet a specified condition CTS>R/$\alpha$, where $\alpha$ denotes a specified scaling factor, and R denotes the range of the portion of the data. Second, the correction factor generator circuit 226 can select IS as the smallest candidate tickmark step within the selected subset of CTSs. In an example, the range R can be computed as the difference between the maximum and the minimum of the specified portion of the medical data, that is, R=max(X)−min(X). In another example, the range can be taken as the largest value of the two: the data span (max(X)−min(X)) and a predetermined minimum allowable display range. Determination of the minimum allowable display range can be dependent on the type of data being displayed. The minimum allowable display range can avoid visual amplification of physiologically insignificant noise in the data. The scaling factor $\alpha$ can be determined using a specified number (TN) of tickmarks and a specified fractional offset (d). In an example, $\alpha$ can be determined as $\alpha = (2*d + TN - 1)$. In an example where TN=3, that is, three tickmarks are to be selected, $\alpha = 2(1+d)$. The fractional offset d represents a buffer between the outer tickmark and the respective bound (LB or UB) for the specified coordinate such as the signal intensity coordinate. In an example, d can be approximately 0.25.

In an example, the correction factor generator circuit 226 can determine the selected tickmark step (TS) without using the plurality of CTS. The correction factor generator circuit 226 can determine an initial tickmark step $TS_0=R/\alpha$, where $\alpha$ can be a scaling factor determined using TN and a specified fractional offset (d). In an example, $\alpha$ can be determined as $\alpha=(2*d+TN-1)$. The correction factor generator circuit 226 can then determine a selected tickmark step (TS) by rounding the initial tickmark step $TS_0$ to a nearest multiple of a specified base resolution (BR) that is greater than $TS_0$. For example, if $TS_0=3$ and BR=2, then TS can be determined as nearest multiples of BR that is greater than $TS_0$, that is, TS=2*BR=4.

The correction factor generator circuit 226 can use the selected TS to determine a correction factor $\delta$ that can be used to compute the desired LB and UB. In an example, the correction factor $\delta$ can be determined as the TS weighted by the scaling factor $\alpha$, that is, $\delta=\alpha*TS$.

In an example, the central tendency measurement circuit 225 can update the initial central tendency measurement $C_0$ by rounding the initial central tendency measure $C_0$ to a nearest multiple of a specified base resolution (BR). The base resolution BR can represent a minimal resolution for the tickmarks. In an example, the specified base resolution BR can be pre-determined, and can be within the range between 0.1 and 5.

In an example, the central tendency measurement circuit 225 can update the initial central tendency measurement $C_0$ using a selected base resolution (BR) chosen from the set of candidate base resolution CBRs. Because each CBR is associated with a respective CTS, the TS as determined by the correction factor generation circuit 226 can correspond to a BR in the set of BRs. In an example, the CTSs can include [0.1, 0.2, 0.3, 0.4, 0.5, 0.6, 0.8, 1, 2, 3, 4, 5, 8, 10, 15, 20, 30, 40, 50], and the BRs can include [0.1, 0.1, 0.1, 0.1, 0.1, 0.2, 0.2, 0.2, 1, 1, 1, 1, 1, 2, 5, 5, 5, 5, 5]. If the correction factor generator circuit 226 determines that TS=0.6, then the correction factor generation circuit 226 can select the corresponding BR=0.2. The correction factor generation circuit 226 can round the initial central tendency $C_0$ to a nearest multiple of the BR, that is, C=round $(C_0/BR)*BR$, where "round" denotes the rounding operator.

The desired LB and UB generator 227 can use the central tendency measure C such as provided by the central tendency measurement circuit 225, and the correction factor $\delta$ such as provided by the correction factor generation circuit 226, to determine the desired bounds LB and UB, respectively. In an example, the LB and UB can be determined as LB=C-$\delta$ and UB=C+$\delta$.

The tickmark generation circuit 228, which can be an embodiment of the tickmark generation circuit 128, can generate the specified number (TN) of tickmarks using inputs from the central tendency measurements circuit 225 and the correction factor generation circuit 226. The tickmarks can be indicative of intermediate levels between the desired bounds LB (which is C-$\delta$) and UB (which is C+$\delta$). In an example, the tickmarks can be equally spaced between the desired LB and UB. The tickmarks can be symmetric around a center between the desired LB and UB. In an example, the specified number TN is independent of the desired range for displaying the medical or physiologic data. In an example, the tickmark generation circuit 228 can generate TN tickmarks including a first tickmark T1 and a second tickmark T2. T1 and T2 are "outer" tickmarks, where T1 is closer to the desired lower bound LB and T2 is closer to the desired upper bound UB. In an example, the first tickmark T1 can be chosen at C-TS*(TN-1)/2, and the second tickmark T2 can be chosen at C+TS*(TN-1)/2. In an example, the first tickmark T1 can be chosen at a specified value LTS, and the second tickmark T2 can be chosen at LTS+TS*(TN-1). In another example, the second tickmark T2 can be chosen at a specified value UTS, and the first tickmark T1 can be chosen at UT-TS*(TN-1). In an example, the tickmark generation circuit 228 can generate three tickmarks, i.e., TN=3. The three tickmarks can include a center tickmark at C, and two outer tickmarks at T1=C-TS and T2=C+TS. In an example, the tickmark generation circuit 228 can additionally generate one or more third tickmarks T3 distributed between T1 and T2 with an inter-tickmark space equal to the selected tickmark step TS.

In an example, the correction factor generator circuit 6 can determine the correction factor $\delta$ as $\delta=TS*d$, and the desired LB and UB generator 227 can use the "outer" tickmarks, T1 and T2, to determine the desired LB and UB, respectively. In an example, the desired LB can be determined as LB=T1-TS*d, and the desired UB can be determined as UB=T2+TS*d. The desired bounds LB and UB, and the generated tickmarks T1, T2, and T3, can be displayed together with the medical or physiologic data.

Figure 3:
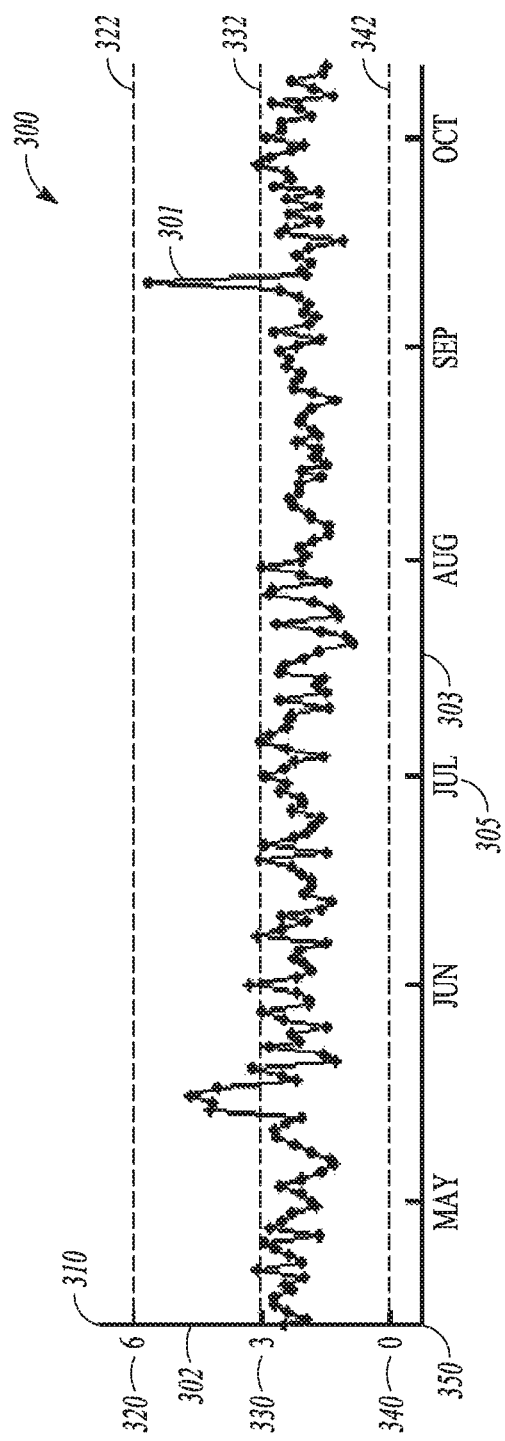
FIG. 3 illustrates an example of a graphical representation of a physiologic trend and the tickmark information.

FIG. 3 illustrates an example of a graphical representation 300 of a physiologic trend and the tickmark information. The graphical representation 300 can be generated using the medical data presentation system 100 or the medical data presentation system 200, and displayed on the display unit 130. The graphical representation of the physiologic trend 301, which can be generated by the graphical representation generator circuit 122, comprises data samples indicative of the intensity of the signal and the line segments connecting the data samples. As illustrated, the physiologic trend 301 can be displayed in a two-dimensional coordinate space spanned by a time axis 303 (show in the abscissa, or the x-axis) and a signal intensity axis 302 (show in the ordinate, or the y-axis). The processor circuit 120 can determine a desired data range on the signal intensity (i.e., the range for displaying the physiologic trend 301) such that the resulting presentation of the physiologic trend 301 can provide an improved visual perception of signal change over time, thereby facilitating data interpretation and clinical decision making.

The desired upper bound (UB) 310 and the desired lower bound (LB) 350 define the range for displaying the physiologic trend 301. In this example, LB=-0.75 and UB=6.75. Also displayed on the y-axis are three tickmarks, including a center tickmark 330 associated with an intermediate level of 3, and two outer tickmarks equally spaced with respect to the center tickmark: a first outer tickmark 320 associated with an intermediate level of 6, and a second outer tickmark 340 associated with an intermediate level of 0. A buffer of 0.25 (corresponding to d as described above) is created between the first outer tickmark 320 and the UB 310, as well as between the second outer tickmark 340 and the LB 350. As illustrated, the display can further include one or more grid lines 322, 332, and 342 associated with the tickmarks 320, 330 and 340, respectively. The grid lines can originate at or cross the respective tickmarks.

Figure 4:
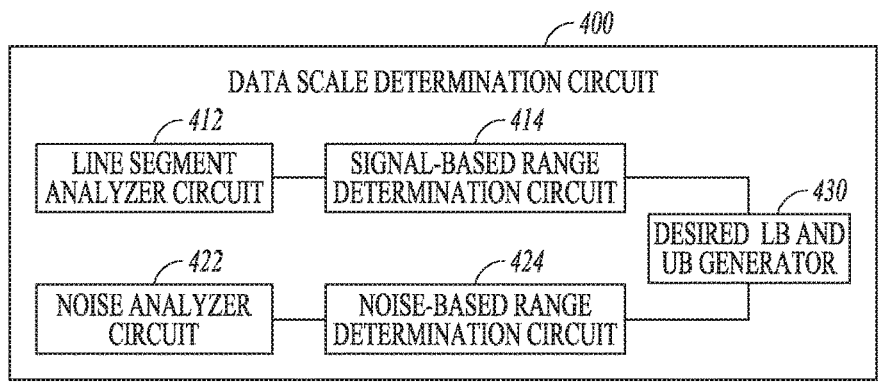
FIG. 4 illustrates an example of a data range determination circuit.

FIG. 4 illustrates an example of a data range determination circuit 400, which can be an embodiment of the data range determination circuit 124. The data range determination circuit 400 can include a line segments analyzer circuit 412, a signal-based range determination circuit 414, a noise analyzer circuit 422, a noise-based range determination circuit 424, and a desired lower bound (LB) and upper bound (UB) generator 430.

The line segments analyzer circuit 412 can generate a plurality of line segments using the medical data. The signal-based range determination circuit 414 can determine a signal-based range using the plurality of line segments.

The signal-based range can include at least one of a signal-based lower bound ($L_S$) or a signal-based upper bound ($U_S$). Examples of the signal-based range determination are described below, such as with reference to FIG. 5.

The noise analyzer circuit 422 can be configured to determine a noise level (N) using the received medical data. In an example, the noise level can be computed as a central tendency of a pair-wise difference of values of the medical data. In another example, the noise level can be computed as a central tendency of differences between the received medical data and a smoothed medical data. The smoothed medical data can be obtained by taking a moving average of the medical data, or by passing the medical data through a low pass filter with specified cutoff frequencies.

The noise-based range determination circuit 424 can determine a noise-based range using at least the noise level (N). The noise-based range can include at least one of a noise-based lower bound ($L_N$) or a noise-based upper bound ($U_N$). In an example, the noise-based range determination circuit 424 can determine $L_N$ and $U_N$ in a two-step process. First, an initial lower bound $L_0$ and an initial upper bound $U_0$ can be determined. In an example, the $L_0$ can be the minimal value of a specified portion of the medical data, and $U_0$ the maximal value of the same specified portion of the medical data. Second, the noise-based range determination circuit 424 can determine the noise-based lower bound $L_N$ using an initial lower bound $L_0$ and a first correction factor $\delta_1$, or to determine the noise-based upper bound $U_N$ using an initial upper bound $U_0$ and a second correction factor $\delta_2$. In an example, the noise-based upper bound $U_N$ can be determined as $U_N = U_0 - \delta_1$, and the noise-based lower bound $L_N$ can be determined as $L_N = L_0 + \delta_2$. The correction factors $\delta_1$ and $\delta_2$ can each be computed using the noise level N, or additionally or alternatively using the initial data range $R_0 = U_0 - L_0$, that is, $\delta_1 = f_1(N, R_0)$ and $\delta_2 = f_2(N, R_0)$, where $f_1$ and $f_2$ are linear or nonlinear functions. In an example, $\delta_1 = \delta_2 = (6*N - R_0)/2$.

The desired LB and UB generator 430 can receive input from the signal-based range determination circuit 414 and the noise-based range determination circuit 424, and generate the desired LB and UB. In an example, the desired LB and UB can each be determined using a comparison of a noise-based range $R_N$ and a signal-based range $R_S$, where $R_N = U_N - L_N$, and $R_S = U_S - L_S$. In an example, the desired LB and UB generator 430 can determine LB to be $L_N$ and UB to be $U_N$ when $R_N$ is greater than $R_S$, and to determine LB to be $L_S$ and UB to be $U_S$ when $R_S$ is greater than $R_N$.

Figure 5:
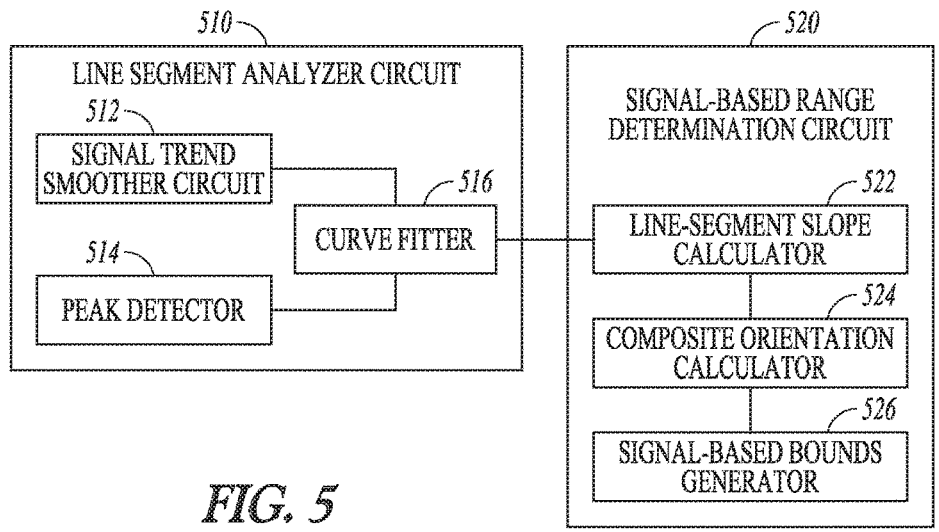
FIG. 5 illustrates an example of a line segment analyzer circuit and a signal-based range determination circuit.

FIG. 5 illustrates an example of the line segment analyzer circuit 510 and signal-based range determination circuit 520, which can be an embodiment of corresponding portions of the data range determination circuit 400. The line segment analyzer circuit 510, which can be an embodiment of the line segments analyzer circuit 412, can include a signal trend smoother circuit 512, a peak detector 514, and a curve fitter 516.

The signal trend smoother circuit 512 can be configured to perform signal smoothing on the received medical data. In an example, the received medical data includes a physiologic trend including physiologic measurements obtained over a sustained period of time, and the signal trend smoother circuit 512 can average the physiologic trend within a specified time window W. For example, the time window W can be approximately 3 days, 7 days, 14 days, or 21 days. The time window can be non-overlapped or overlapped, and the resulting averaged physiologic trend can represent a smoothed physiologic trend. In another example, the signal trend smoother circuit can include a filter, such as a low pass filter with specified cutoff frequencies.

The peak detector 514 can detect the peaks and troughs of the smoothed medical data. The curve fitter 516 can take the original non-smoothed medical data, or the smoothed medical data, and generate a plurality of line segments. In an example, the curve fitter 516 can perform curve fitting using a specified number of data samples from the non-smoothed or smoothed medical data. In another example, the curve fitter 516 can perform curve fitting using some or all data samples between a detected trough and a neighboring detected peak. Examples of the curve fitting methods can include linear regression model based on least squares approach, among other methods.

The signal-based range determination circuit 520, which can be an embodiment of the signal-based range determination circuit 414, can include a line-segment slope calculator 522, a composite orientation calculator 524, and a signal-based bounds generator 526. The line-segment slope calculator 522 can determine, for one or more of the line segments, respective one or more line-segment slopes. A line-segment slope $m_i$ can indicate an orientation $\theta_i$ of the line segment $l_i$ in the coordinate space. The orientation $\theta_i$ can be related to the $m_i$ by $m_i = \tan(\theta_i)$.

The composite orientation calculator 524 can compute a composite orientation ($\theta_{Avg}$) using the orientations $\{\theta\} = \{\theta_1, \theta_2, \ldots, \theta_K\}$ of all or a selected number (K) of the line segments. $\theta_{Avg}$ can be a linear or a nonlinear combination of the $\{\theta\}$. In an example, $\theta_{Avg}$ computed as a weighted sum: $\theta c = a_1\theta_1 + a_2\theta_2 + \ldots + a_K\theta_K$, where the weights $\{a_1, a_2, \ldots, a_N\}$ can each be proportional to the length of the respective line segment. For example, $\theta_{Avg} = l_1\theta_1 + l_2\theta_2 + \ldots + l_K\theta_K$.

The signal-based bounds generator 526 can generate the signal-based lower bound $L_S$ and the higher bound $H_S$. Because Ls and Hs can define the edges of the display region (such as 310 and 350 in FIG. 3), values of $L_S$ and $H_S$ can determine the data range ($R_S = Hs - Ls$), which may impact the slop m for the line segments displayed between Ls and Hs. For example, for a line segment having an orientation $\theta$ between 0 and 90 degrees, an increase in $R_S$ can cause the line segment to be vertically "stretched", resulting in a steeper slope and increased angle $\theta$. Conversely, a decrease in $R_S$ can cause the line segment to be vertically "compressed", resulting in a more moderate slope and decreased angle $\theta$. Therefore, the line segment slope m can be a function of the range $R_S$ of a display. The signal-based bounds generator 526 can determine a desired data range $R_S$ and therefore at least one of the $L_S$ or the $U_S$, in response to the composite orientation ($\theta_{Avg}$) meeting a specified criterion. In an example, the signal-based bounds generator 526 can determine the $R_S$, and therefore at least one of the $L_S$ or the $U_S$, such that the composite orientation ($\theta_{Avg}$) of all the line segments is 45 degrees. Line segment with an orientation of 45 degrees can provide an improved visual perception of the change in the line-segment, and average orientation of 45 degrees can maximize the discriminability of adjacent line segments.

Figure 6:
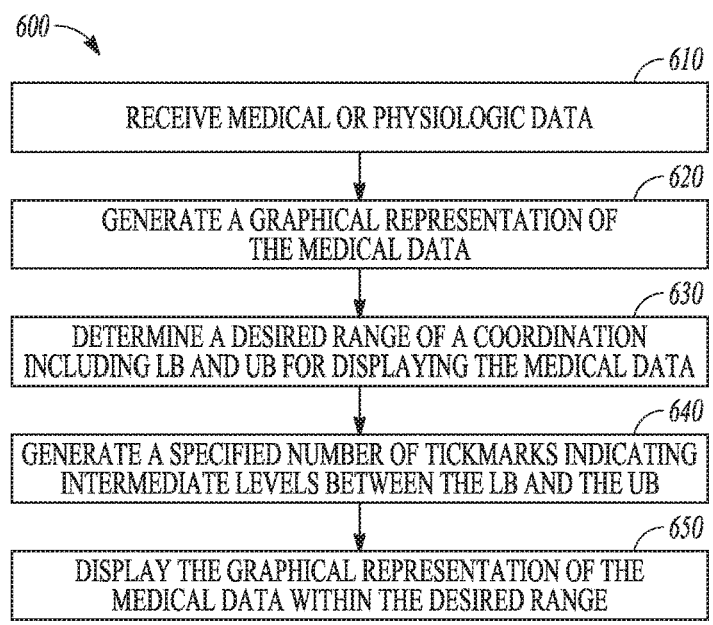
FIG. 6 illustrates an example of a method for displaying medical data in a two-dimensional or higher-dimensional coordinate space.

FIG. 6 illustrates an example of a method 600 for displaying medical data in a two-dimensional or higher-dimensional coordinate space. The method 600 can be implemented in a patient management system communicating with an implantable, wearable, or other ambulatory medical device. In an example, the method 600 can be performed by the medical data presentation system 100, or any modification thereof.

The method 600 can begin at step 610, where medical or physiologic data can be received. The medical or physiologic data can include a trend comprising data obtained at different time instants or time intervals. In an example, the medical data receiver 111 can receive physiologic signals indicative of worsening of heart failure (HF). The medical data can be sensed using physiologic sensors, or be retrieved from a data storage device such as an electronic medical record (EMR) system.

At 620, a graphical representation of the medical data can be generated. The medical data can be generated in a two-dimensional or a higher-dimensional coordinate space. In an example, the received medical data can include a physiologic trend, and the coordinate space can be a two-dimensional coordinate space spanned by a time axis and a signal intensity axis. The graphical representation can comprise line segments indicating temporal variation of the received medical or physiologic data. In an example, the line segments can be generated using curve-fitting of two or more measured samples of the physiologic trend.

At 630, a desired range of axis, such as the intensity axis of a physiologic trend, can be determined. The range can include a desired lower bound LB and a desired upper bound UB for displaying the medical data. The range as defined by the LB and UB can affect the orientation of the line-segments. For example, an increased range (i.e., a wider range between LB and UB) can cause the line segments of the displayed data to be vertically "stretched", while a reduced range (i.e., a narrower range between LB and UB) can cause the line segments to be vertically "compressed." When the LB and UB are properly selected, the line segments can be oriented such that they can render enhance visual perception of signal change. This can be beneficial to clinicians in interpreting the medical data or making diagnosis and treatment decisions. In an example, an initial desired bounds LB and UB can first be determined. Then, a correction factor can be chosen to expand, reduce, or otherwise modify the initial decision of the LB or UB. In an example, the LB and UB can be determined using the statistical properties of the medical data, or noise characteristics presented in the medical data. Examples of determining the desired range, including the LB and UB, are discussed below, such as with reference to FIGS. 7 and 8.

At 640, a specified number (TN) of tickmarks can be generated. The tickmarks can include a graphical mark, or a numerical indicator indicating intermediate levels of intensity of the medical data between the LB and UB. In an example, the tickmarks can be equally spaced between the desired LB and UB. The tickmarks can be symmetric around a center between the desired LB and UB. The specified number TN can be independent of the desired range for displaying the medical or physiologic data. In an example, at least three tickmarks can be generated, including a center tickmark located at or near the center between LB and UB, a tickmark at or near LB, and a tickmark at or near UB.

At 650, the graphical representation of the medical data, including the line segments, can be displayed in a display unit such as computer monitor or other types of display screen. The graphical representation can be limited within the desired range, such as between the desired lower bound LB and the desired upper bound UB. In an example, one or more of the tickmarks can be displayed together with the line segments. In an example, one or more grid lines respectively originating at or crossing the plurality of tickmarks can also be displayed. The display unit can include a user interface that comprises user controls allowing interactive selection, adjustment, highlighting, not addition, or other operations on the displayed information.

Figure 7:
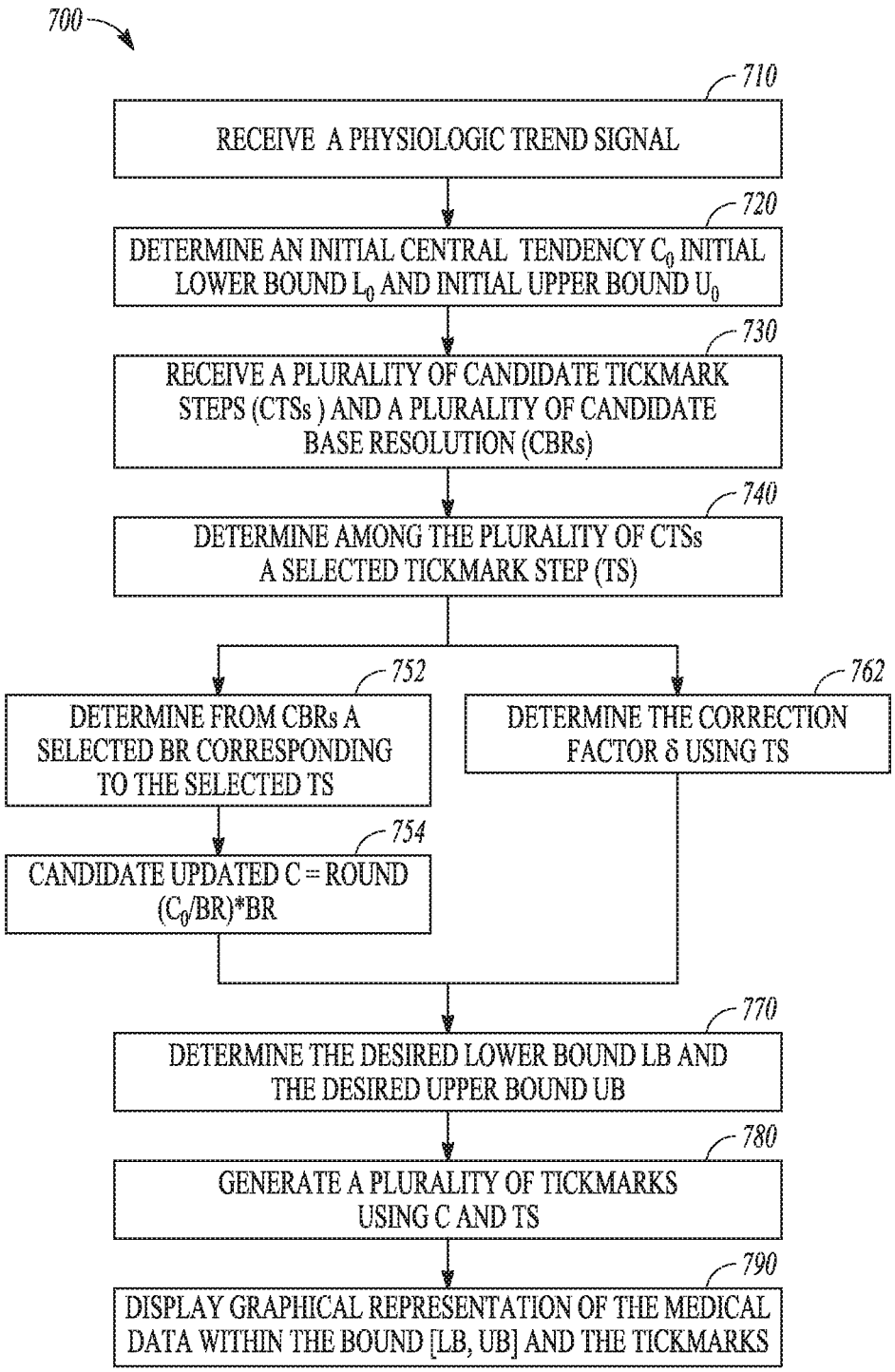
FIG. 7 illustrates an example of a method for displaying medical data in a range determined based on signal statistics.

FIG. 7 illustrates an example of a method 700 for displaying medical data in a range determined based on signal statistics. The method 700 can be an embodiment of the method 600. As illustrated, a physiologic trend signal can be received at 710. The physiologic trend can comprise samples of a physiologic signal, such as electrocardiogram, intracardiac electrogram, arrhythmia, heart rate signal, heart rate variability signal, intrathoracic impedance signal, intracardiac impedance signal, arterial pressure signal, pulmonary artery pressure signal, left atrial pressure signal, RV pressure signal, LV coronary pressure signal, coronary blood temperature signal, blood oxygen saturation signal, one or more heart sounds signal, physical activity or exertion level signal, physiologic response to activity, posture, respiration signal, body temperature measurements, among other physiologic signals.

At 720, one or more signal statistics can be obtained from the received physiologic trend. This may include an initial central tendency measure $C_0$, initial lower bound $L_0$, and initial upper bound $U_0$. In an example, the initial lower bound $L_0$ can be computed as the minimum of a specified portion of the medical data, and the initial upper bound $U_0$ can be computed as the maximum of the specified portion of the medical data, max(X). The initial central tendency measure $C_0$ can be computed as an average between $L_0$ and $U_0$, that is, $C_0=(\max(X)+\min(X))/2$.

At 730, a plurality of candidate tickmark steps (CTSs) and a corresponding plurality of candidate base resolutions (CBRs) can be received. The CTS can include a plurality of values that each indicating a step size (e.g., a minimal change) at the corresponding tickmark. The CBRs can include a plurality of values that indicate a base resolution at the center of the tickmark. Each CBR can correspond to a particular CTS. The number of the CTSs can be equal to the number of the CBRs. In an example, the CTSs can include [0.1, 0.2, 0.3, 0.4, 0.5, 0.6, 0.8, 1, 2, 3, 4, 5, 8, 10, 15, 20, 30, 40, 50]. In an example, the CBRs can include [0.1, 0.1, 0.1, 0.1, 0.1, 0.2, 0.2, 0.2, 1, 1, 1, 1, 1, 2, 5, 5, 5, 5, and 5].

At 740, a selected tickmark step (TS) can be select from the plurality of CTSs when the TS meets a specified criterion. In an example, the TS can be determined by first choosing from the CTSs a subset of the CTSs that meet the meet a specified condition $CTS>R/\alpha$, where $\alpha$ denotes a specified scaling factor, and $R=(U_0-L_0)$ denotes the range of the received physiologic trend. Then, the selected TS can be selected as the smallest candidate tickmark step within the selected subset of CTSs. The scaling factor $\alpha$ can be determined using a specified number (TN) of tickmarks and a specified fractional offset (d). In an example, $\alpha$ can be determined as $\alpha=(2*d+TN-1)$. In an example where TN=3, that is, three tickmarks are to be selected, $\alpha=2(1+d)$. The fractional offset d represents a buffer between the outer tickmark and the respective bound (LB or UB) for the specified coordinate such as the signal intensity coordinate. In an example, d can be approximately 0.25.

In an example, the selected tickmark step (TS) can be determined without using the plurality of CIS. An initial tickmark step $TS_0$ can be chosen as $TS_0=R/\alpha$, where $\alpha$ can a scaling factor determined using TN and a specified fractional offset (d). In an example, $\alpha$ can be determined as $\alpha=(2*d+TN-1)$. The selected tickmark step (TS) can then be determined by rounding the initial tickmark step $TS_0$ to a nearest multiple of a specified base resolution (BR) that is greater than $TS_0$.

The selected TS can then be used at 752 to determine a corresponding base resolution (BR), among the plurality of CBRs, which corresponds to the TS in the plurality of CTSs. At 754, the initial central tendency $C_0$ can be updated to a nearest multiple of the BR, that is, C=round $(C_0/BR)*BR$, where "round" denotes the rounding operator. In another example, a specified base resolution BR can be pre-determined, and the initial central tendency measurement $C_0$ can be updated by rounding the initial central tendency measure $C_0$ to a nearest multiple of BR.

The selected TS can be used at 762 to determine a correction factor $\delta$. In an example, the correction factor $\delta$ can be TS weighted by the scaling factor $\alpha$, that is, $\delta=\alpha*TS$.

At 770, the central updated central tendency measure C' as decided at 754 and the correction factor $\delta$ determined at 762 can be used to determine the desired bounds LB and UB, respectively. In an example, the LB and UB can be determined as LB=C−$\delta$ and UB=C+$\delta$.

At 780, a specified number (TN) tickmarks can be generated, which indicate intermediate levels between the desired bounds LB and UB. The specified number TN can be independent of the desired range for displaying the medical or physiologic data. In an example, the tickmarks can be equally spaced between the desired LB and UB. The tickmarks can be symmetric around a center between the desired LB and UB. In an example, the tickmarks can include a first tickmark T1 and a second tickmark T2. T1 and T2 are "outer" tickmarks, where T1 is closer to the desired lower bound LB and T2 is closer to the desired upper bound UB. In an example, the first tickmark T1 can be chosen at C−TS*(TN−1)/2, and the second tickmark T2 can be chosen at C+TS*(TN−1)/2. In an example, the first tickmark T1 can be chosen at a specified value LTS, and the second tickmark T2 can be chosen at LTS+TS*(TN−1). In another example, the second tickmark T2 can be chosen at a specified value UTS, and the first tickmark T1 can be chosen at UTS−TS*(TN−1). In an example, at least three tickmarks can be generated, corresponding to three intermediate levels, including a center tickmark at C, and two outer tickmarks at C−TS and C+TS. In an example, the tickmarks can additionally include one or more third tickmarks T3 distributed between T1 and T2 with an inter-tickmark space equal to the selected tickmark step TS.

In an example, the desired LB and UB can be determined using the "outer" tickmarks, T1 and T2, respectively. In an example, the desired LB can be determined as LB=T1−TS*d, and the desired UB can be determined as UB=T2+TS*d. At 790, graphical representation of the medical data, together with the tickmarks, can then be generated within the bounds defined by LB and UB.

Figure 8:
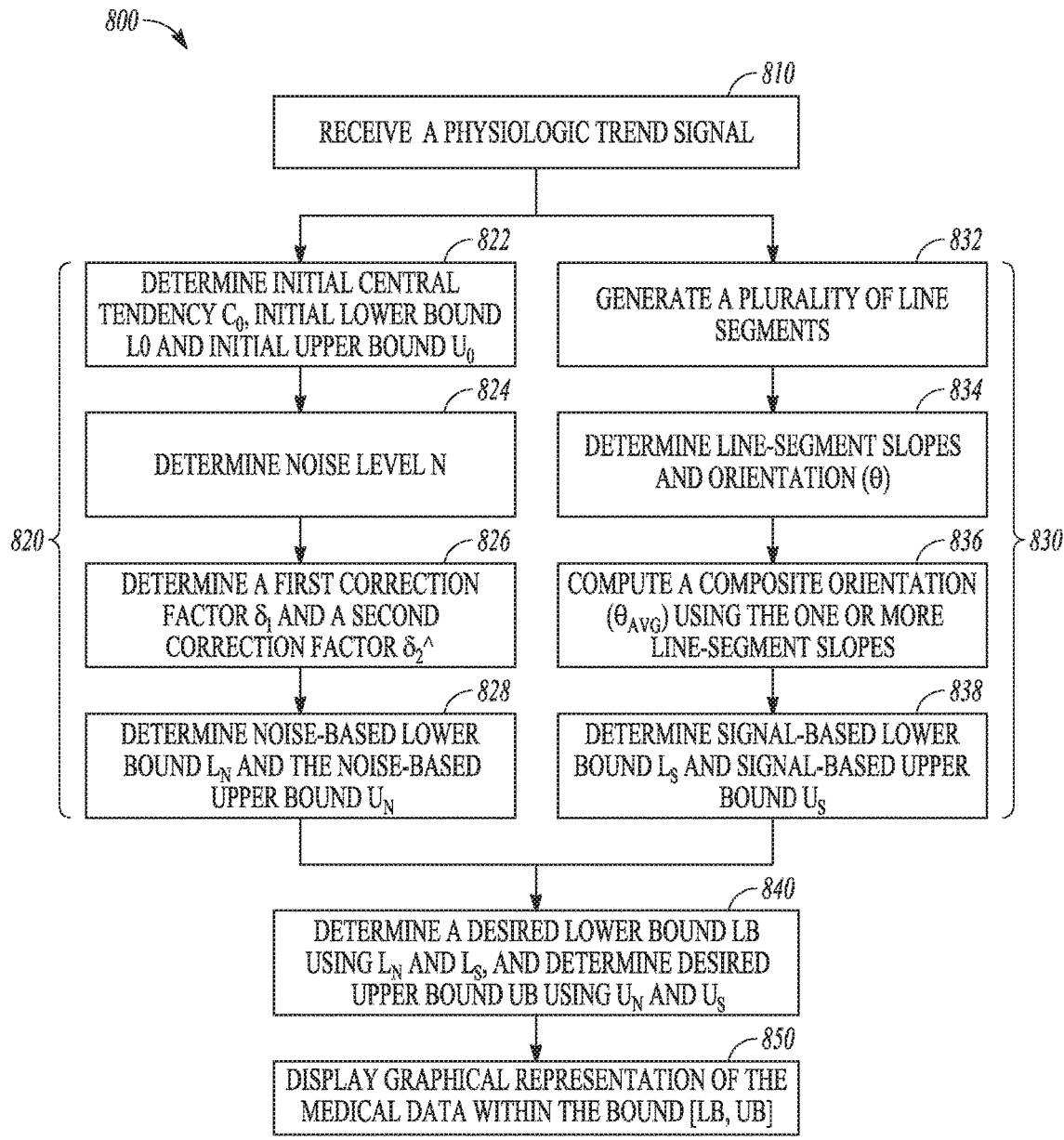
FIG. 8 illustrates an example of a method for displaying medical data in a range determined based on noise characteristics and optimal line segment orientation.

FIG. 8 illustrates an example of a method 800 for displaying medical data in a range determined based on noise characteristics and optimal line segment orientation. The method 800 can be an embodiment of the method 600. The method 800 can begin at 810 by receiving a physiologic trend signal. The received physiologic trend can then be processed through two paths: a path 820 and a path 830. The path 820, including steps 822 through 828, can determine a noise-based range. At 822, an initial central tendency $C_0$, an initial lower bound $L_0$, and an initial upper bound $U_0$ can be determined, such as by using similar approaches as described at 720. At 824, a noise level (N) can be determined from the physiologic trend signal. The noise level (N) can be computed as a central tendency of a pair-wise difference of values of the medical data, or a central tendency of differences between the received medical data and a smoothed medical data such as obtained using moving average or low pass filtering of the received data.

At 826, correction factors 61 and 62 can each be determined using the noise level N, or additionally or alternatively using the initial data range $R_0=U_0-L_0$, that is, $\delta_1=f_1(N, R_0)$ and $\delta_2=f_2(N, R_0)$, where $f_1$ and $f_2$ are linear or nonlinear functions. In an example, $\delta_1=\delta_2=(6*N-R_0)/2$.

At 828, noise-based lower bound $L_N$ and the noise-based upper bound $U_N$ can be respectively determined using the initial lower bound $L_0$, the initial upper bound $U_0$, and the correction factors $\delta_1$ and $\delta_2$. In an example, the noise-based upper bound $U_N$ can be determined as $U_N=U_0-\delta_1$, and the noise-based lower bound $L_N$ can be determined as $L_N=L_0+\delta_2$.

The path 830 can determine a signal-based range, which can include steps 832 through 838. At 832, a plurality of line segments can be generated by using the received medical data, such as by using a curve fitting method based on least squares approach. Line-segment slopes can be computed for one or more of the line segments at 834. A line-segment slope $m_i$ can indicate an orientation $\theta_i$ of the line segment $l_i$ in the coordinate space. The orientation $\theta_i$ can be related to the $m_i$ by $m_i=\tan(\theta_i)$.

At 836, a composite orientation ($\theta_{Avg}$) can be computed using the orientations $\{\theta\}=\{\theta_1, \theta_2, \ldots, \theta_K\}$ of all or a selected number (K) of the line segments. $\theta_{Avg}$ can be a linear or a nonlinear combination of the $\{\theta\}$. In an example, $\theta_{Avg}$ computed as a weighted sum: $\theta c=a_1\theta_1+a_2\theta_2+\ldots+a_N\theta_K$, where the weights $\{a_1, a_2, \ldots, a_N\}$ can each be proportional to the length of the respective line segment. For example, $\theta_{Avg}=l_1\theta_1+l_2\theta_2+\ldots+l_K\theta_K$.

At 838, a desired data range $R_S$, and therefore at least one of the $L_S$ or the $U_S$, can be determined in response to the composite orientation ($\theta_{Avg}$) meeting a specified criterion. In an example, the $R_S$, and thus the $L_S$ or the $U_S$, can be determined such that the composite orientation ($\theta_{Avg}$) of all the line segments is 45 degrees. Line segment with an orientation of 45 degrees can provide an improved visual perception of the change in the line-segment, and average orientation of 45 degrees can maximize the discriminability of adjacent line segments.

At 840, the desired LB and UB can be respectively determined using a comparison of the noise-based range indicating a range ($R_N$) between the $L_N$ and $U_N$ and the signal-based range indicating a range ($R_S$) between the $L_S$ and $U_S$. In an example, if $R_N$ is greater than $R_S$, the LB can be determined to be $L_N$ and UB to be $U_N$. However, if $R_S$ is greater than $R_N$, then LB can be determined to be $L_S$ and UB to be $U_S$. The graphical representation of the medical data can then be generated within the bounds defined by LB and UB.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for displaying medical or physiologic data, comprising:
   an input circuit, configured to receive medical or physiologic data;
   a processor circuit, configured to:
   generate a graphical representation of the medical or physiologic data in a two-dimensional or a higher-dimensional coordinate space, the graphical representation including line segments indicating temporal variation of the medical or physiologic data; and
   determine a display range of at least one axis for displaying the medical or physiologic data, including determining a lower bound (LB) and an upper bound (UB) using an initial signal statistical parameter and a correction factor ($\delta$), wherein the correction factor $\delta$ is computed using at least one of a signal range of the received medical or physiologic data, a specified number of tickmarks for the at least one axis, or a noise level of the received medical or physiologic data; and
   a display unit, coupled to the processor unit, configured to display in the coordinate space the graphical representation of the medical or physiologic data within the determined display range.

2. The system of claim 1, wherein the processor circuit is further configured to generate a specified number (TN) of tickmarks equally spaced between the determined LB and UB and symmetric around a center between the determined LB and UB, and the display unit is configured to display the specified number of tickmarks.

3. The system of claim 1, wherein:
   the medical or physiologic data include a physiologic trend signal; and
   the processor circuit is configured to generate a graphical representation of the physiologic trend signal in a two-dimensional coordinate space.

4. The system of claim 1, wherein the initial signal statistical parameter includes an initial central tendency measure ($C_0$) of a specified portion of the medical or physiologic data to be displayed.

5. The system of claim 2, wherein the processor circuit is configured to:
   receive a plurality of candidate tickmark steps (CTSs); and
   determine a selected tickmark step (TS) from the plurality of CTSs, the selected tickmark step TS being the smallest among the CTSs that satisfies CTS>R/$\alpha$, wherein R indicates a range of the specified portion of the medical or physiologic data and $\alpha$ is a scaling factor determined using TN and a specified fractional offset (d).

6. The system of claim 2, wherein the processor circuit is configured to:
   determine an initial tickmark step $TS_0=R/\alpha$, wherein $\alpha$ is a scaling factor determined using TN and a specified fractional offset (d); and
   determine a selected tickmark step (TS) including rounding the initial tickmark step $TS_0$ to a nearest multiple of a specified base resolution (BR), the nearest multiple of BR greater than $TS_0$.

7. The system of claim 5, wherein the processor circuit is configured to:
   determine the correction factor $\delta$ as $\delta=TS*\alpha$; and
   determine the LB as LB=C−$\delta$ and the UB as UB=C+$\delta$, where C is an updated central tendency measure of the specified portion of the medical or physiologic data to be displayed.

8. The system of claim 4, wherein the processor circuit is configured to determine an updated central tendency C including rounding the initial central tendency measure $C_0$ to a nearest multiple of a selected base resolution (BR).

9. The system of claim 5, wherein the processor circuit is configured to:

receive a plurality of candidate base resolution (CBRs), each CBR corresponding to a respective candidate tickmark step in the CTSs; and determine a selected base resolution (BR) among the plurality of CBRs corresponding to the selected TS; and determine an updated central tendency C including rounding the $C_0$ to a nearest multiple of the BR.

10. The system of claim 9, wherein the processor circuit is configured to:

generate the specified number (TN) of tickmarks including a first tickmark T1 and a second tickmark T2;

determine the correction factor $\delta$ as $\delta=TS*d$; and determine the LB as $LB=T1-\delta$ and the UB as $UB=T2+\delta$;

wherein the first tickmark T1 and the second tickmark T2 are such that:

T1 is at $C-TS*(TN-1)/2$ and T2 is at $C+TS*(TN-1)/2$;

T1 is at a specified value LTS, and T2 is at $LTS+TS*(TN-1)$; or

T2 is at a specified value UTS, and T1 is at $UTS-TS*(TN-1)$.

11. The system of claim 1, further comprising:

a noise analyzer circuit configured to determine a noise level using the medical or physiologic data, and to determine a noise-based range using at least the noise level, the noise-based range including at least one of a noise-based lower bound ($L_N$) or a noise-based upper bound ($U_N$); and a line segment analyzer circuit configured to generate a plurality of line segments using the medical or physiologic data, and to determine a signal-based range using the plurality of line segments, the signal-based range including at least one of a signal-based lower bound ($L_S$) or a signal-based upper bound ($U_S$);

wherein the processor circuit is configured to determine the display range including the determined lower bound LB or the determined upper bound UB using one or more of $L_N$, $U_N$, $L_S$, or $U_S$.

12. The system of claim 11, wherein:

the initial signal statistical parameter includes an initial lower bound $L_0$ and an initial upper bound $U_0$, the $L_0$ indicating a minimal value of a specified portion of the medical or physiologic data, and $U_0$ indicating a maximal value of the specified portion of the medical or physiologic data;

the correction factor includes a first correction factor Si and a second correction factor $\delta_2$, the first and second correction factors $\delta_1$ and $\delta_2$ each determined using the noise level;

the noise analyzer circuit is configured to determine the noise-based lower bound $L_N$ using an initial lower bound $L_0$ and a first correction factor $\delta_1$, or to determine the noise-based upper bound $U_N$ using an initial upper bound $U_0$ and a second correction factor $\delta_2$.

13. The system of claim 11, wherein the line segment analyzer circuit is configured to:

determine for one or more of the line segments respective one or more line-segment slopes, the line-segment slopes indicative of an orientation ($\theta$) of the respective line segment;

compute a composite orientation ($\theta_{Avg}$) using the one or more line-segment slopes corresponding to the plurality of the line segments;

determine at least one of the signal-based lower bound ($L_S$) or the signal-based upper bound ($U_S$) in response to the composite orientation ($\theta_{Avg}$) meeting a specified criterion.

14. A method of operating a system to display medical or physiologic data, comprising:

receiving medical or physiologic data using an input circuit;

generating a graphical representation of the medical or physiologic data in a two-dimensional or a higher-dimensional coordinate space using a processor circuit, wherein the coordinate space includes a time coordinate, and the graphical representation includes line segments indicating temporal variation of the medical or physiologic data;

determining a display range of at least one axis for displaying the medical or physiologic data using the processor circuit, including determining at least one of a lower bound (LB) or an upper bound (UB) using an initial signal statistical parameter and a correction factor ($\delta$), the correction factor $\delta$ computed using at least one of a signal range of the received medical or physiologic data, a specified number of tickmarks for the at least one axis, or a noise level of the received medical or physiologic data; and displaying, on a display unit, the graphical representation of the medical or physiologic data within the determined display range in the coordinate space.

15. The method of claim 14, further comprising:

generating a specified number (TN) of tickmarks equally spaced between the determined LB and UB and symmetric around a center between the determined LB and UB; and displaying, on a display unit, the specified number of tickmarks.

16. The method of claim 15, wherein the initial signal statistical parameter includes an initial central tendency measure ($C_0$) of a specified portion of the medical or physiologic data to be displayed.

17. The method of claim 15, further comprising:

receiving a plurality of candidate tickmark steps (CTSs); and determining a selected tickmark step (TS) from the plurality of CTSs, the selected tickmark step TS being the smallest among the CTSs that satisfies $CTS>R/\alpha$, wherein R indicates a range of the specified portion of the medical or physiologic data and $\alpha$ is a scaling factor determined using TN and a specified fractional offset (d).

18. The method of claim 17, wherein:

receiving a plurality of candidate base resolution (CBRs), each CBR corresponding to a respective candidate tickmark step in the CTSs;

determining a selected base resolution (BR) among the plurality of CBRs corresponding to the selected TS;

determining an updated central tendency C including rounding the $C_0$ to a nearest multiple of the BR;

generating the specified number (TN) of tickmarks including a first tickmark T1 and a second tickmark T2;

determine the correction factor $\delta$ as $\delta=TS*d$; and determine the LB as $LB=T1-\delta$ and the UB as $UB=T2+\delta$;

wherein the first tickmark T1 and the second tickmark T2 are such that:

T1 is at $C-TS*(TN-1)/2$ and T2 is at $C+TS*(TN-1)/2$;

T1 is at a specified value LTS, and T2 is at $LTS+TS*(TN-1)$; or

T2 is at a specified value UTS, and T1 is at $UTS-TS*(TN-1)$.

19. The method of claim 14, wherein determining the display range includes:

determining a noise level using the medical or physiologic data;

determining a noise-based range using at least the noise level, the noise-based range including at least one of a noise-based lower bound ($L_N$) or a noise-based upper bound ($U_N$);

generating a plurality of line segments using the medical or physiologic data;

determining a signal-based range using the plurality of line segments, the signal-based range including at least one of a signal-based lower bound ($L_S$) or a signal-based upper bound ($U_S$); and determining the display range including the lower bound LB or the upper bound UB using one or more of $L_N$, $U_N$, $L_S$, or $U_S$.

20. The method of claim 19, wherein determining the signal-based range includes:

determining for one or more of the line segments respective one or more line-segment slopes, the line slopes indicative of an orientation ($\theta$) of the respective line segment;

computing a composite orientation ($\theta_{Avg}$) using the one or more line-segment slopes corresponding to the plurality of the line segments; and determining at least one of the signal-based lower bound ($L_S$) or the signal-based upper bound ($U_S$) in response to the composite orientation ($\theta_{Avg}$) meeting a specified criterion.

* * * * *